US011344208B2

(12) United States Patent
Aoyagi et al.

(10) Patent No.: US 11,344,208 B2
(45) Date of Patent: May 31, 2022

(54) BLOOD PRESSURE MEASURING APPARATUS, WRIST WATCH TYPE TERMINAL HAVING THE SAME, AND METHOD OF MEASURING BLOOD PRESSURE

(71) Applicant: SAMSUNG ELECTRONICS CO., LTD., Suwon-si (KR)

(72) Inventors: Yosuke Aoyagi, Yokohama (JP); Takeshi Nagahiro, Yokohama (JP); Takahiro Tokumiya, Yokohama (JP)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 846 days.

(21) Appl. No.: 16/157,635

(22) Filed: Oct. 11, 2018

(65) Prior Publication Data

US 2019/0038152 A1    Feb. 7, 2019

Related U.S. Application Data

(62) Division of application No. 14/812,040, filed on Jul. 29, 2015, now abandoned.

(30) Foreign Application Priority Data

Mar. 5, 2015    (KR) .................. KR10-2015-0031116

(51) Int. Cl.
*A61B 5/021*        (2006.01)
*A61B 5/00*         (2006.01)
(Continued)

(52) U.S. Cl.
CPC ........ *A61B 5/02108* (2013.01); *A61B 5/0075* (2013.01); *A61B 5/0082* (2013.01);
(Continued)

(58) Field of Classification Search
CPC ...... A61B 5/02; A61B 5/02255; A61B 5/0261
See application file for complete search history.

(56) References Cited

U.S. PATENT DOCUMENTS

2007/0016085 A1*    1/2007   Inukai ................ A61B 5/02125
                                                                600/485
2009/0204011 A1     8/2009   Suzuki
                  (Continued)

FOREIGN PATENT DOCUMENTS

JP          11-155826 A      6/1999
JP          2000-225097 A    8/2000
                  (Continued)

OTHER PUBLICATIONS

Communication dated Oct. 2, 2018, issued by the Japanese Patent Office in counterpart Japanese Application No. 2014-216125.
(Continued)

*Primary Examiner* — Puya Agahi
(74) *Attorney, Agent, or Firm* — Sughrue Mion, PLLC

(57) ABSTRACT

Provided is a blood pressure measuring apparatus, a wrist watch type terminal, and a method of measuring blood pressure. The blood pressure measuring apparatus includes a light source that emits light onto a living body, a light receiver that receives light from the living body, and a signal processing device that calculates the blood pressure based on a detected signal received from the light receiver, wherein the signal processing device includes a subtractor that obtains a subtraction value by subtracting a moving average value of the detected signal in a second duration which is shorter than a first duration from a moving average value of the detection signal in the first duration, an extractor that extracts a feature point of a pulse wave based on the
(Continued)

subtraction value, and a converter that converts a feature amount obtained based on the feature point to a blood pressure value.

9 Claims, 9 Drawing Sheets

(51) Int. Cl.
    *A61B 5/024*     (2006.01)
    *A61B 5/02*     (2006.01)
    *A61B 5/026*     (2006.01)
    *A61B 5/0225*     (2006.01)

(52) U.S. Cl.
    CPC ...... *A61B 5/02416* (2013.01); *A61B 5/02438* (2013.01); *A61B 5/7235* (2013.01); *A61B 5/7278* (2013.01); *A61B 5/02* (2013.01); *A61B 5/0261* (2013.01); *A61B 5/02255* (2013.01); *A61B 5/681* (2013.01); *A61B 5/742* (2013.01)

(56) References Cited

U.S. PATENT DOCUMENTS

| | | |
|---|---|---|
| 2011/0077531 A1 | 3/2011 | Watson et al. |
| 2012/0215118 A1* | 8/2012 | Chen ............... A61B 5/022 600/490 |
| 2012/0277548 A1 | 11/2012 | Burton |
| 2013/0324866 A1 | 12/2013 | Gladshtein |
| 2015/0216425 A1* | 8/2015 | Gladshtein ........... A61B 8/0891 600/431 |
| 2016/0128582 A1* | 5/2016 | Chod ................... A61B 5/0295 600/473 |

FOREIGN PATENT DOCUMENTS

| | | |
|---|---|---|
| JP | 2002-369805 A | 12/2001 |
| JP | 2007-007075 A | 1/2007 |
| JP | 2007-98002 A | 4/2007 |
| JP | 2008-302127 A | 12/2008 |
| JP | 2011-167424 A | 9/2011 |
| JP | 2013-056083 A | 3/2013 |
| JP | 2013-153845 A | 8/2013 |
| JP | 5466115 B2 | 4/2014 |
| JP | 5549092 B2 | 7/2014 |
| JP | 2014-151010 A | 8/2014 |
| KR | 10-2010-0033875 A | 3/2010 |

OTHER PUBLICATIONS

Communication dated Nov. 26, 2019, issued by the Japanese Patent Office in counterpart Japanese Application No. 2018-247726.
Communication dated May 22, 2018, issued by the Japanese Patent Office in counterpart Japanese Application No. 2014-216125.
Communication dated Jul. 21, 2021, issued by the Korean Intellectual Property Office in Korean Patent Application No. 10-2015-0031116.

* cited by examiner

BLOOD PRESSURE MEASURING APPARATUS, WRIST WATCH TYPE TERMINAL HAVING THE SAME, AND METHOD OF MEASURING BLOOD PRESSURE

CROSS-REFERENCE TO RELATED APPLICATIONS

This application is a divisional of U.S. patent application Ser. No. 14/812,040, filed on Jul. 29, 2015 in the U.S. Patent and Trademark Office and claims priority from Japanese Patent Application No. 2014-216125, filed on Oct. 23, 2014 in the Japanese Intellectual Property Office, and Korean Patent Application No. 10-2015-0031116, filed on Mar. 5, 2015 in the Korean Intellectual Property Office, the disclosures of which are incorporated herein in their entireties by reference.

BACKGROUND

1. Field

Apparatuses and methods consistent with exemplary embodiments relate to blood pressure measuring apparatuses, wrist watch type terminals having the same, and methods of measuring blood pressure.

2. Description of the Related Art

A blood pressure measuring apparatus may detect an amount of reflection light in a blood vessel as a photoelectric wave by radiating near infrared rays thereto. In particular, the blood pressure measuring apparatus may include a photoelectric sensor and a body movement sensor, and remove unnecessary frequency components of the photoelectric sensor and the body movement sensor. Blood pressure is calculated by using a ratio of output values of the photoelectric sensor and a pressure sensor as a calibration value.

In the photoelectric blood pressure measuring apparatus, a pulse wave is measured in such a manner that a white noise or an alternating current (AC) component that is generated from a circuit is added to the pulse wave besides an AC component which is the intrinsic feature of the pulse wave. Accordingly, components besides the pulse wave of a living body are included as noise.

In particular, when a wrist watch type blood pressure measuring apparatus is used as a blood pressure measuring apparatus instead of a cuff type blood pressure measuring apparatus, a mounting state of the blood pressure measuring apparatus is changed due to a movement of a measuring subject or an external disturbance. Accordingly, the amount of noise increases, and thus, improvement of measurement precision is difficult. Furthermore, a systolic blood pressure 2 (SBP2) may be difficult to measure since the variation of a pulse wave is small.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a blood pressure measuring apparatus that may precisely measure blood pressure, and method of measuring the blood pressure.

According to an aspect of an exemplary embodiment, there is provided a blood pressure measuring apparatus including: a light receiver configured to receive light reflected from a living body; and a signal processing device that is configured to measure a blood pressure from a pulse wave detected from the received light and include: a subtractor configured to obtain a subtraction value by subtracting a moving average value of the detected pulse wave in a second duration which is shorter than a first duration from a moving average value of the detected pulse wave in the first duration; an extractor configured to extract a feature point of the pulse wave based on the subtraction value; and a converter configured to convert the extracted feature amount obtained based on the feature point to a blood pressure value.

The signal processing device may specify a cycle of the pulse wave based on the subtraction value, the pulse wave having a plurality of cycles, may obtain a plurality of feature amounts by extracting the feature point respectively in each of the plurality of cycles of the pulse wave, and may calculate the blood pressure from the plurality of feature amounts.

The signal processing device may exclude one of the plurality of cycles from which the feature point is not extracted due to noise from the calculating of the blood pressure.

According to another aspect of an exemplary embodiment, a blood pressure measuring apparatus includes: a sensor including a light source configured to emit light onto a living body and a light receiver configured to receive light from the living body, the received light carrying a first detection signal and a second detection signal and being represented as a pulse wave; and a signal processing device configured to extract a first feature point and a second feature point of the pulse wave based on the first detection signal and the second detection signal and convert a feature amount of the pulse wave to a blood pressure value based on the extracted first feature point and the extracted second feature point of the pulse wave, wherein the light source is further configured to output the first detection signal based on light of a first wavelength range and the second detection signal based on light of a second wavelength range that is shorter than the first wavelength range, and the signal processing device is further configured to extract the first feature point based on a systolic blood pressure (SBP) that is based on the first detection signal in a first duration of the pulse wave, extract the second feature point based on the second detection signal in a second duration which is a duration different from the first duration, and convert the feature amount into the blood pressure value based on the first and second feature points.

The second feature point may include a maximum value and a minimum value of a single pulse wave.

The light of the first wavelength range may be red light or infrared light, and the light of the second wavelength range may be green light.

The light source alternately may emit the light of the first wavelength range suring the first duration and the light of the second wavelength range during the second duration.

According to another aspect of an exemplary embodiment, a method of measuring a blood pressure by using a blood pressure measuring apparatus that includes a light source that emits light onto a living body, a light receiver that receives light from the living body, and a signal processing device that measures blood pressure based on a detection signal which is received from the light receiver and represented by a pulse wave, the method including: obtaining a subtraction value by subtracting a moving average value of the detection signal in a second duration from a moving average value of the detection signal in a first duration which is shorter than the second duration; extracting a feature point of the pulse wave based on the subtraction value; and converting a feature amount that is obtained based on the feature point to a blood pressure value.

The first duration may be one cycle of a power source being used, and the second duration may be 1 to 5 cycles of the pulse wave.

According to another aspect of an exemplary embodiment, a method of measuring blood pressure by using a blood pressure measuring apparatus that includes a sensor including a light source that emits light onto a living body, and a light receiver that receives light from the living body, the received light carrying a first detection signal and a second detection signal and being represented as a pulse wave, and a signal processing device that extracts a first feature point and a second feature point of the pulse wave based on the first detection signal and the second signal received from the sensor, and converts feature amounts based on the first feature point and the second feature point to a blood pressure value, the method includes: outputting the first detection signal based on light of a first wavelength range and the second detection signal based on light of a second wavelength range which is shorter than the first wavelength range; extracting the first feature point of the pulse wave in a first duration of a cycle of the pulse wave based on an SBP that is obtained based on the first detection signal, and the second feature point based on the second detection signal in a second duration that is different from the first duration in the cycle; and converting the feature amounts that are obtained based on the first and second feature points to the blood pressure value.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
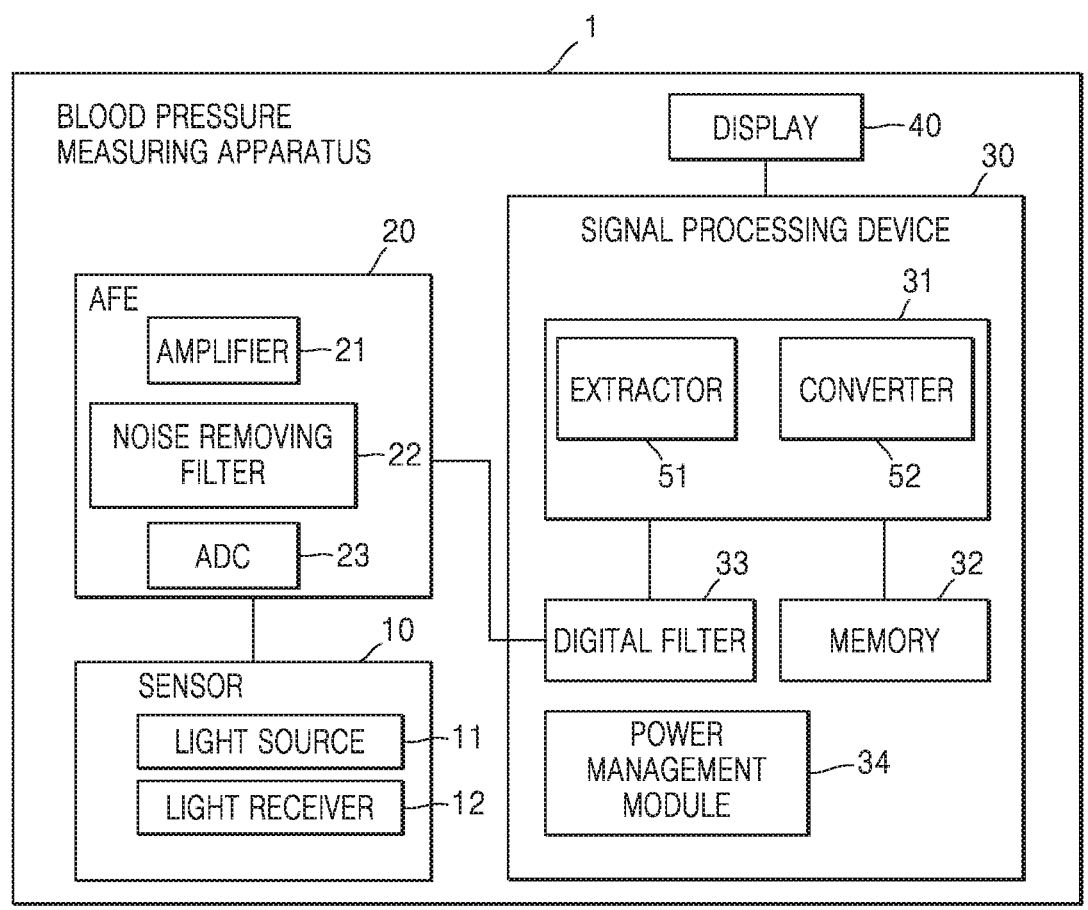
FIG. 1 is a block diagram of a configuration of a blood pressure measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Embodiment 1

A blood pressure measuring apparatus according to an exemplary embodiment will be described with reference to FIG. 1. FIG. 1 is a block diagram of a configuration of a blood pressure measuring apparatus 1 according to an exemplary embodiment. The blood pressure measuring apparatus 1 includes a sensor 10, an analogue front end (AFE) 20, a signal processing device 30, and a display 40. The blood pressure measuring apparatus 1 may be, for example, a measuring device installed on a wearable type terminal, and may be mounted on a wrist of an object (a human) by using a strap or a band. That is, the strap surrounds around an arm, and thus, a blood pressure measuring state is achieved by using the blood pressure measuring apparatus 1.

The sensor 10 includes a light source 11 and a light receiver 12. The light source 11 may be a light-emitting device, for example, a light-emitting diode (LED), and may emit green light, red light, or infrared light. Light emitted from the light source 11 is radiated onto a living body.

The light receiver 12 may be a light detector, for example, a charge coupled device (CCD) or a complementary metal oxide semiconductor (CMOS) image sensor, and is disposed near the light source 11. The light receiver 12 receives light from a living body, and outputs a detected signal corresponding to the intensity of the received light to the AFE 20. Accordingly, the sensor 10 is a photoelectric sensor that detects a volume pulse wave corresponding to a volume change of a blood vessel.

More specifically, when light emitted from the light source 11 is radiated onto a living body, the light is scattered at an epidermis, a thick skin, a capillary vessel, a peripheral blood vessel, a fat, and an artery of the living body. The light receiver 12 detects the scattered light at various portions of the living body. A pulse flowing in the blood vessel moves at a constant time duration, and a feature movement is observed from the intensity (pulse wave) of the scattered light obtained from the pulse. That is, the intensity of the scattered light indicates a pulse wave. A living body index, such as a blood pressure, an oxygen content in blood, an augmentation index (AI) value, etc. may be obtained by interpreting the pulse wave.

The light source 11 may emit red light or infrared light that readily passes through a skin surface or a thick surface of a living body. Accordingly, the intensity of scattered light that is scattered in a blood vessel of a living body may be increased. The light receiver 12 may be disposed to receive light passing through the living body. At this point, the light source 11 and the light receiver 12 are disposed to face each other with the living body therebetween.

The AFE 20 includes an amplifier 21, a noise removing filter 22, and an analog digital converter (ADC) 23. The amplifier 21 amplifies a detected signal that is transmitted from the sensor 10. The noise removing filter 22 is an analog filter and removes noise of the detected signal that is amplified at the amplifier 21. The noise removing filter 22 may be an LC filter, such as a low pass filter or a high pass filter. The ADC 23 converts the detected signal from which noise has been removed at the noise removing filter 22 to a digital signal. Next, the ADC 23 outputs the detected signal that has been converted to a digital signal to the signal processing device 30. The ADC 23 outputs a digital value that is sampled at a predetermined sampling duration as a detected signal.

The signal processing device 30 may be, for example, a microcomputer and may include a central processing unit (CPU) 31, a memory 32, digital filter 33, and a power management module 34. The memory 32 stores a predetermined program. The CPU 31 reads and executes the program stored in the memory 32. In this manner, according to the detected signal at the AFE 20, a systolic blood pressure (SBP) and a diastolic blood pressure (DBP) may be measured. In order to measure a blood pressure, as described below, the CPU 31 performs a processing for extracting a feature point and a processing for converting a feature amount to a blood pressure. Accordingly, as depicted in FIG. 1, the CPU 31 may include an extractor 51 that extracts the feature point and a converter 52 that converts the feature amount to the blood pressure. Also, the signal processing device 30 may calculate a health index, for example, the AI value besides the blood pressure.

The power management module 34 controls power supplied to the sensor 10. For example, the power management module 34 allows the light source 11 to emit light at a predetermined intensity by supplying a driving current to the light source 11. Also, the power management module 34 may control the light source 11 to emit light at a predetermined intermittent duration by controlling the current supplying time.

Figure 2:
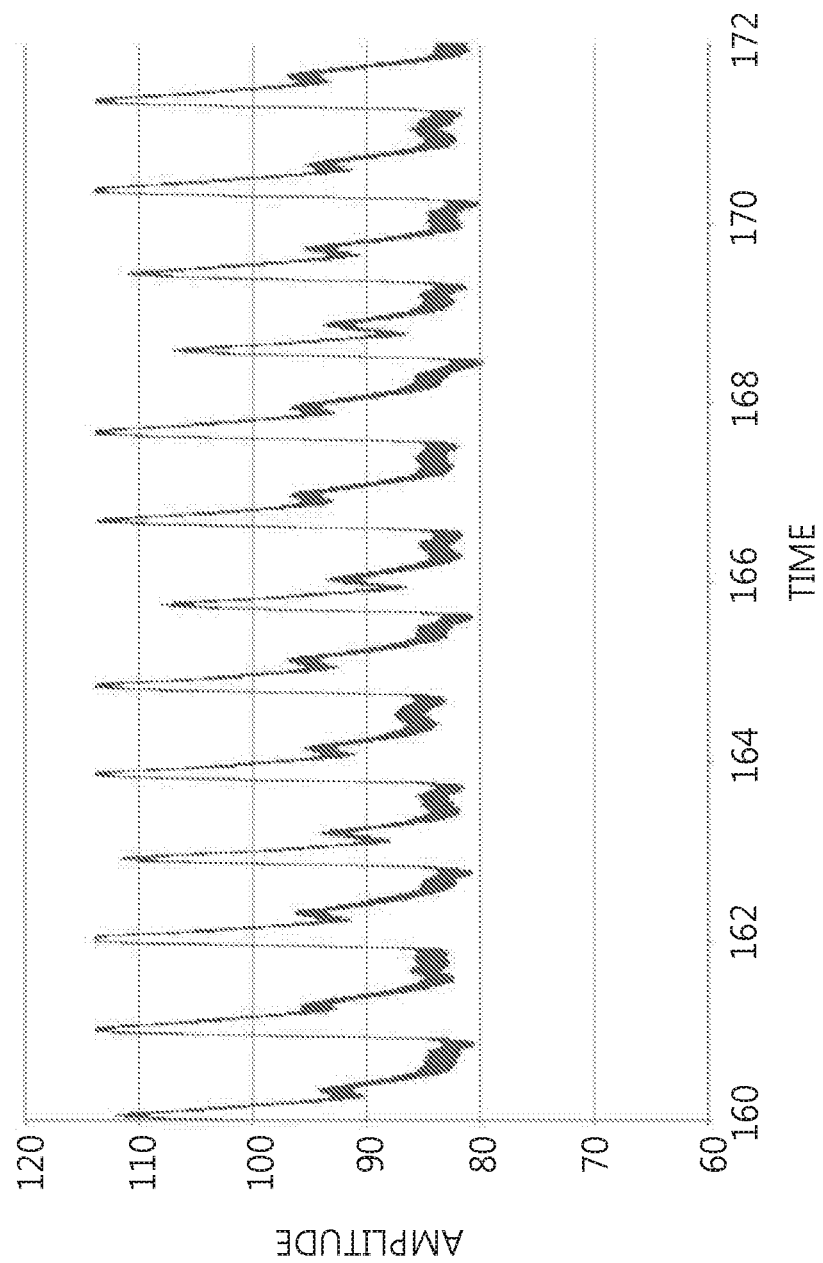
FIG. 2 is a graph showing an example of a signal detected at a sensor of a blood pressure measuring apparatus according to an exemplary embodiment.

FIG. 2 is a graph showing a detected signal that is outputted from the AFE 20. As depicted in FIG. 2, a pulse wave according to a vascular pulsation is repeatedly appeared as a detected signal. Also, the detected signal includes white noise or circuit noise that is generated at an electronic circuit. The digital filter 33 performs a digital processing that removes a noise component from the detected signal. Also, the CPU 31 measures a blood pressure in response to the detected signal from which the noise has been removed by the digital filter 33.

The digital filter 33 obtains a moving average with respect to the detected signal. In order to obtain a moving average $a(n)$ at an arbitrary time $t(n)$, all data in periods of $[t(n-m) \sim t(n+m)]$ including data before and after the arbitrary time $t(n)$ is added, and the added value is divided by $2m+1$. First, the digital filter 33 calculates a moving average of a first duration corresponding to a frequency of a power source as a first moving average. For example, a duration corresponding to a 1 cycle (50 Hz or 60 Hz) of a commercial power source is determined as the first duration, and then, the digital filter 33 obtains an average digital included in the first duration.

Next, the digital filter 33 calculates a second moving average from the moving average of a second duration which is longer than the first duration. For example, the second duration is selected according to the pulse wave. A longer section than a single pulse is selected as the second duration. Here, as a practical example, a duration corresponding to one cycle of 0.47 Hz may be selected as the second duration. That is, the digital filter 33 obtains an average of digital value included in 1/0.47 Hz. Since the second duration is longer than the first duration, the number of data included in the second duration is greater than the number of data included in the first duration. Accordingly, the second moving average has a smaller variation than the first moving average.

Figure 3A:
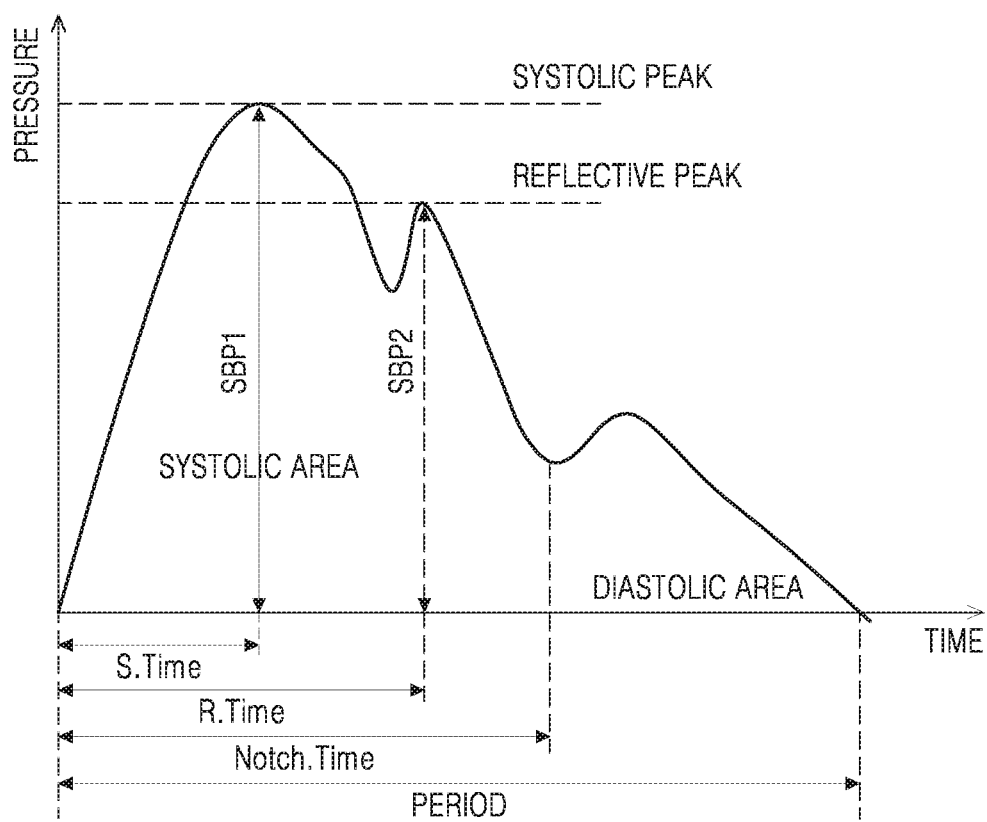
FIGS. 3A and 3B are graphs showing an example of a pulse wave from which noise is removed by using a digital filter and feature points of the pulse wave measured by a blood pressure measuring apparatus according to an exemplary embodiment.
Figure 3B:
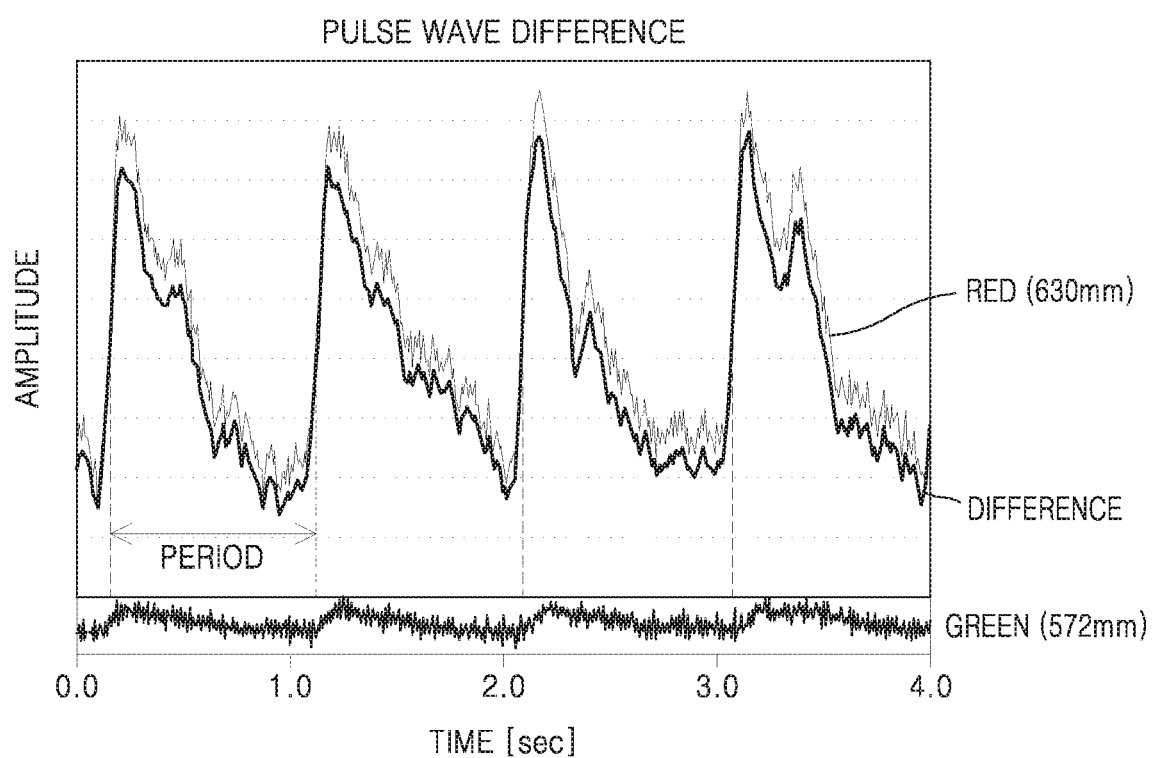

Also, the digital filter 33 is a subtractor that calculates a subtraction value which is calculated by subtracting the second moving average value from the first moving average value. FIG. 3A is a graph showing an example of waveform of a subtraction value calculated from the first moving average value and the second moving average value. FIG. 3A also shows an example of a subtraction value and a feature point extracted from the subtraction value, and a magnified view of an ideal pulse wave. FIG. 3B is a graph respectively showing different pulse waves between a pulse wave obtained by red light and a pulse wave obtained from green light. Here, a subsequent computation process is performed by using the result of the red light. An infrared light may be used instead of the red light.

The signal processing device 30, as depicted in FIGS. 3A and 3B, may specify a first cycle of a pulse wave from the time when the subtraction value is positive. In the following descriptions, a pulse wave of one cycle is referred to as a single pulse wave. The signal processing device 30 may set a time when the subtraction value is changed from negative to positive as a beginning point of the single pulse wave.

Next, the extractor 51 of the signal processing device 30 extracts a feature point of the single pulse wave according to the subtraction value. The signal processing device 30 extracts, for example, a first maximum value, a first minimum value, a second maximal value, a second minimal value, and an inflection point as feature points at every single pulse wave. The signal processing device 30 may calculate a value and a time of the feature point from the waveform of the subtraction value. For example, the signal processing device 30 calculates the feature point through calculating a pulse wave velocity by differentiating the pulse wave or calculating an acceleration pulse wave by differentiating the pulse wave twice. FIG. 3A shows an example of the feature point extracted by the signal processing device 30.

In FIG. 3A, a first peak (maximum value) is a systolic peak and a second peak (maximal value) is a reflective peak in the first cycle. A minimal value after the second peak is a notch that indicates a boundary between a systole and a diastole. A time from the beginning point of the cycle to the systolic peak is determined as an S. time. A time from the beginning point of the cycle to a reflective peak is determined as an R. time. A time from the beginning point of the cycle to the notch is determined as a notch time. The signal processing device 30 extracts a minimum value as a feature point. In this manner, the signal processing device 30 calculates values and times of the feature points. Also, the maximum value and the minimum value may be calibrated based on the subtraction value at the notch.

The signal processing device 30 calculates feature amounts from the values and times of a plurality of the feature points included in a single pulse wave. The feature amounts denotes values for calculating an SBP and a DBP and are values derived from the values and times of the feature points in the single pulse wave. The feature amounts may be calculated by an equation that is set in advance. The values of the feature amounts vary according to the variation of a blood pressure, and uses values that greatly varies with respect to the blood pressure, and thus, the blood pressure may be precisely measured. Also, in the feature points, the subtraction value may be referred to as the feature amounts. Here, since both the SBP and the DBP are to be obtained, two equations are needed.

Figure 4A:
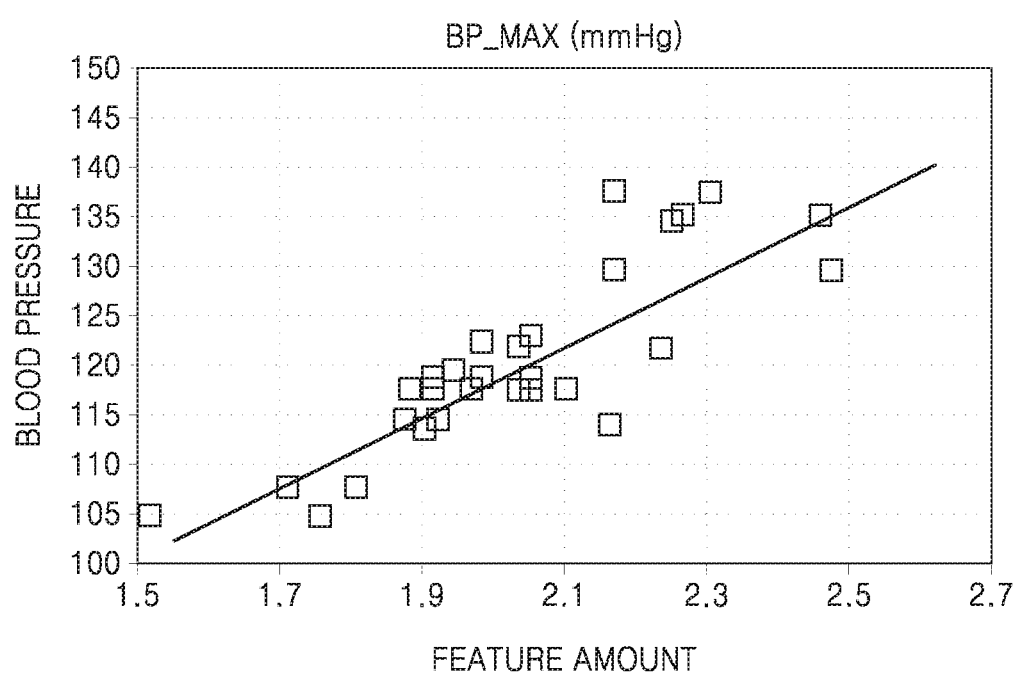
FIGS. 4A and 4B are graphs showing linear regressions for converting a feature amount of a feature point extracted from a pulse wave that is measured by a blood pressure measuring apparatus to a blood pressure according to an exemplary embodiment.
Figure 4B:
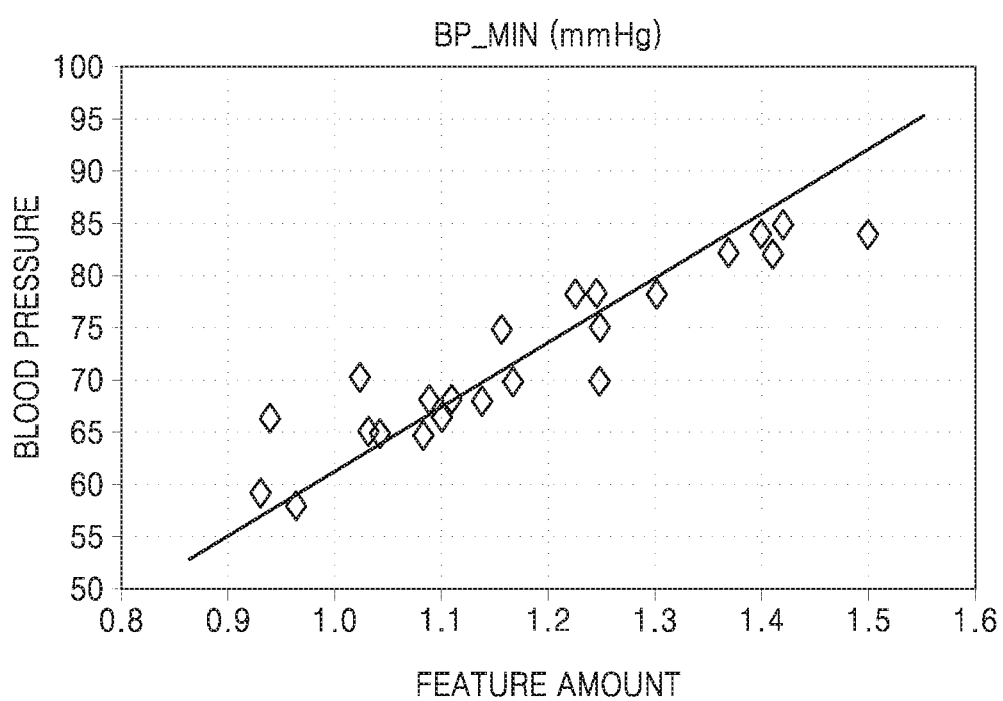

Next, the converter 52 of the signal processing device 30 converts the feature amounts to the blood pressure. The converter 52 converts the feature amounts to the blood pressure by using a linear regression. Here, as shown in FIGS. 4A and 4B, in order to calculate the SBP BP_MAX and the DBP BP_MIN, two linear regressions are stored in the memory 32. The signal processing device 30 calculates the feature amount for the SBP and the feature amount for the DBP based on the single pulse wave. The signal processing device 30 calculates the SBP from a pre-determined feature amount by using the linear regression for the SBP. Also, the signal processing device 30 calculates a DBP from another feature amount by using the linear regression for the DBP. In this manner, a blood pressure is measured by using the blood pressure measuring apparatus 1. The extracted feature points and equations for calculating the feature amounts from the feature points may be optimized by using a well-known method. That is, the feature points and the equations for precisely measuring the blood pressure are set.

The linear regression is set by using a plurality of measuring results that are obtained in advance. That is, feature amounts are obtained by using the blood pressure measuring apparatus 1 according to the exemplary Embodiment 1 with respect to a plurality of subjects, and at the same time, a blood pressure is measured by using a cuff type blood pressure measuring apparatus. Thus a data base of the feature amounts corresponding to the blood pressure value is constructed. Then, a linear regression is obtained by performing a regression analysis with respect to the recorded data base. The linear regression may be set according to sex and age, for example, males in their 20s, females in their 20s, males in their 30s, females in their 30s, etc. That is, after obtaining data for sex and age, a data base may be constructed. The signal processing device 30 may convert the feature amounts to the blood pressure by using not only a linear regression but also a regression curve that uses a polynomial expression, for example, a second-degree polynomial expression or more.

Also, the signal processing device 30 may calculate a blood pressure based on a plurality of pulse waves. For example, the signal processing device 30 may calculate feature amounts after extracting feature points with respect to n number (n is an integer more than 2) of pulse waves. In this manner, since the feature amounts are calculated for every single pulse wave, feature amounts of n numbers are calculated. Next, the signal processing device 30 converts the n feature amounts to an SBP or a DBP respectively by using the linear regression. In this manner, blood pressures of n numbers are calculated. An average of the n numbers of blood pressures may be regarded as a blood pressure. In this manner, when the feature amounts are calculated based on a plurality of pulse waves, a measuring accuracy may be improved.

Also, a blood pressure may be obtained by excluding some of the n numbers of blood pressures. For example, a blood pressure may be obtained from an average of n−2 numbers of blood pressures by excluding the maximum and minimum blood pressures from the n numbers of blood pressures. Accordingly, a blood pressure measuring accuracy may be improved. Also, a pulse wave having big different values of feature amounts or feature points from other pulse waves may be excluded from the calculation of the blood pressure.

A single pulse wave (one cycle) from which feature points may not be extracted may be excluded from the calculation of the blood pressure. For example, when a maximal value or a minimal value that are required for calculating feature amounts are buried in noise due to an effect of the noise, the feature amounts may not be calculated from the corresponding cycle. Accordingly, the blood pressure may not be converted from the single pulse wave (cycle) from which feature points may not be extracted. In this manner, an accuracy of the blood pressure may be improved.

In this manner, the signal processing device 30 determines the feature points, such as a first maximum value, a first minimum value, a second maximal value, and a second minimal value by determining rising or falling characteristics of a pulse wave based on a subtraction value. Also, the signal processing device 30 may calculate the feature amounts from a plurality of feature points for every single pulse wave. The signal processing device 30 may convert the feature amounts to a blood pressure by using a linear regression that is set in advance.

The display 40 includes a display monitor, such as a liquid crystal display. The display 40 displays a waveform of a pulse wave that is calculated by the signal processing device 30.

The blood pressure measuring apparatus 1 utilizes a subtraction value between a moving average of a first duration and a moving average of a second duration. In this way, the effect of diffusing noise besides an external disturbance light, vibration, and a pulse may be reduced. Accordingly, a precision of measuring a blood pressure may be improved by appropriately extracting feature points. Also, a duration corresponding to a frequency (50 Hz or 60 Hz) of a commercial power source may be used as a first moving average value. In this manner, power source noise may be reduced.

Also, the digital filter 33 may reduce noise by digital processing the noise. Accordingly, a blood pressure measuring apparatus may be simply manufactured when compared to using an analog filter. For example, when noise is removed by using the analog filter, it is necessary to design a circuit for the analog filter of a device where the analog filter is used. In the current exemplary embodiment, noise is removed through processing a digital signal by a computer program, and thus, a blood pressure measuring apparatus may have simple structure.

Moreover, the signal processing device 30 specifies 1 cycle (a single pulse wave) of a pulse wave by using the subtraction value. That is, a beginning time of 1 cycle is specified at a time when the subtraction value is 0. In this way, a further appropriate feature amounts may be obtained. For example, since a time from the beginning time to a feature point may be precisely obtained, an appropriate feature amounts may be obtained. A first moving average value and a second moving average value are obtained based on a detected signal of a single light receiver 12. In this manner, it is possible to appropriately estimate a noise level. Also, a further higher precision measurement is possible. If a subtraction value is obtained by frequently calculating a moving average, a high precision measurement is possible even though noise is changed.

Figure 5:
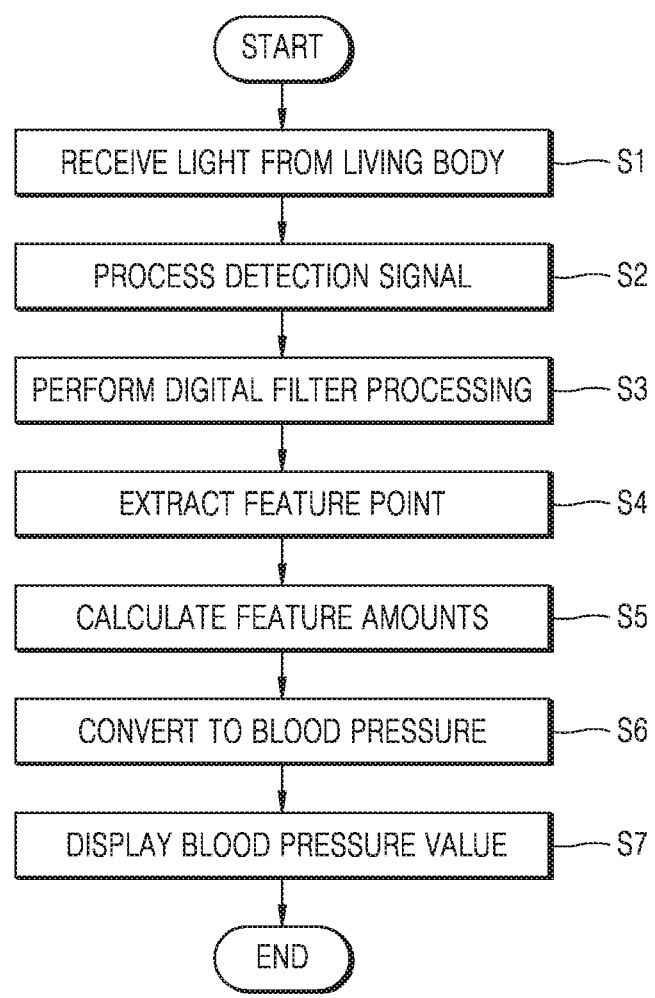
FIG. 5 is a flow chart of a method of measuring a blood pressure according to an exemplary embodiment.

A method of measuring a blood pressure according to the exemplary Embodiment 1 is described with reference to FIG. 5, which shows a flow chart of a method of measuring a blood pressure.

First, the blood pressure measuring apparatus 1 is mounted on a part of a measurement subject (living body), for example, a wrist, and light emitted from a living body (wrist) is received by using the light receiver 12 (S1). The light receiver 12 performs a photoelectric conversion of a signal that indicates an intensity of the received light and outputs the conversion result to the AFE 20.

Next, the AFE 20 processes a detected signal inputted from the sensor 10 (S2). As described above, the amplifier 21 of the AFE 20 amplifies the detected signal. The noise removing filter 22 filters the detected signal and removes noise. The ADC 23 performs an AD conversion of the detected signal.

The digital filter 33 performs a digital filter processing with respect to the detected signal (S3). That is, noise is removed by obtaining a subtraction value between a first moving average value and a second moving average value. Also, a cycle may be specified by the subtraction value.

The signal processing device 30 extracts a feature point based on the subtraction values (S4). For example, the signal processing device 30 may extract the feature point by differentiating or differentiating twice a pulse wave that is appeared by the subtraction value. Here, the signal processing device 30 extracts feature points on every single pulse wave. That is, the signal processing device 30 calculates the feature amounts on every single pulse wave based on values and times of the feature points (S5). That is, the signal processing device 30 converts the values and times of the feature points to the feature amounts by using an equation that is set in advance. The feature amounts are not calculated from a pulse wave from which feature points are not extracted.

Next, the signal processing device 30 converts the feature amounts to a blood pressure by using a linear regression (S6). The signal processing device 30 calculates a SBP and a DBP. The display 40 displays the obtained blood pressure (S7). Through these processes, the effects described above may be obtained.

Also, when a bio information besides the blood pressure is to be measured, it is necessary to set an equation and a linear regression for obtaining a feature amount according to bio information of the measurement subject (living body). For example, when blood oxygen saturation is measured, an equation is determined for calculating a feature amount from a feature point and a value of the feature point, etc. A data base is constructed by measuring the blood oxygen saturation with respect to a plurality of measurement subjects in advance. Next, a linear regression is obtained according to the data base. In this manner, blood oxygen saturation may be measured by using the blood pressure measuring apparatus 1.

Embodiment 2

Figure 6:
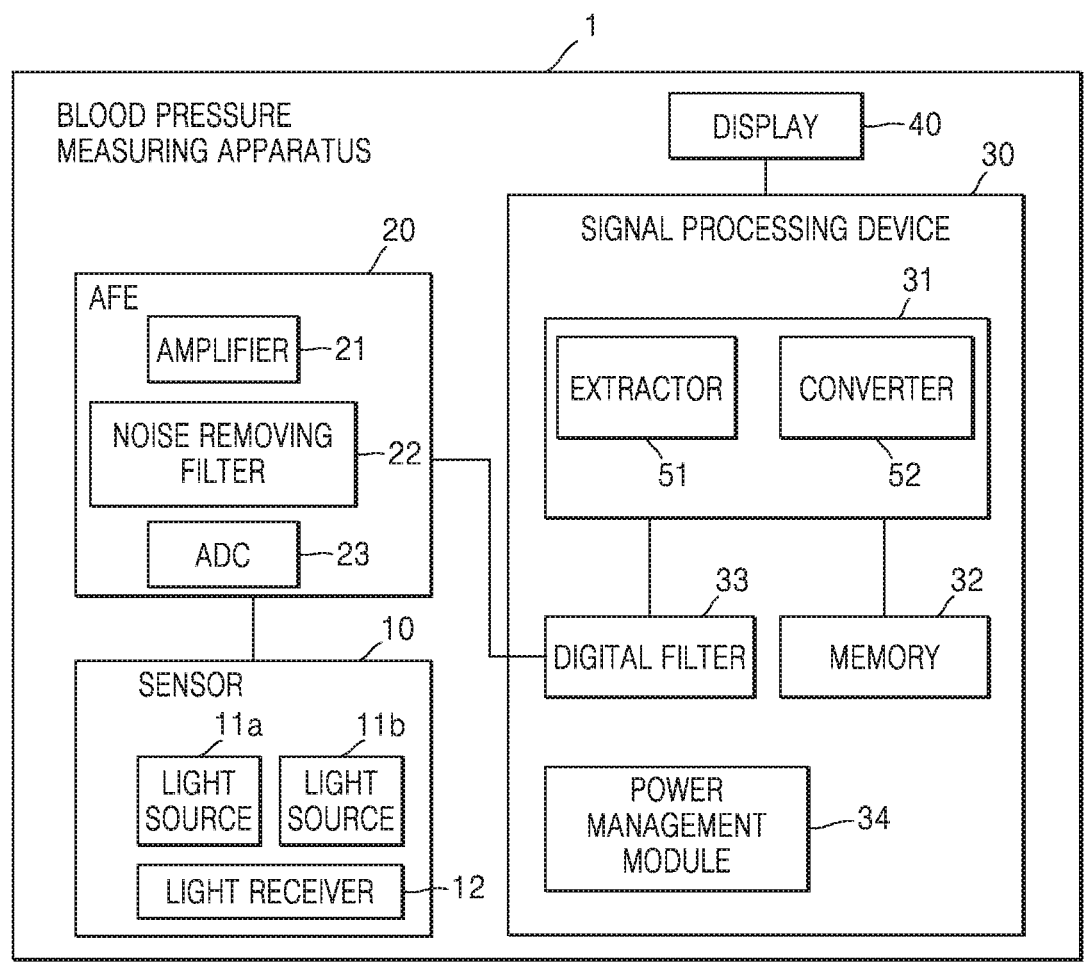
FIG. 6 is a block diagram of a configuration of a blood pressure measuring apparatus according to another exemplary embodiment.

A blood pressure measuring apparatus according to another exemplary embodiment will be described with reference to FIG. 6. FIG. 6 is a block diagram of a configuration of a blood pressure measuring apparatus. In the current exemplary embodiment, a feature point corresponding to a SBP2 is extracted. The SBP2 is a systolic rear blood pressure and corresponds to the reflective peak of a systolic period of FIG. 3A. The SBP2 is a feature point that exists before a notch after SBP1 of a single pulse wave, and is used as an important index of bio-information from which hardness (AI value) of a blood vessel may be derived. However, the SBP2 is difficult to extract since the variation of a pulse wave is small.

A configuration for extracting a feature point of the SBP2 will be described. In the current exemplary embodiment, in order to extract the feature point of the SBP2, two light sources, that is, a first light source 11a and a second light source 11b are installed on the sensor 10. The basic configuration and processing of the blood pressure measuring apparatus 1 are the same as the exemplary embodiment, and thus, the description will not be repeated.

In the current exemplary embodiment, the sensor 10 includes the first light source 11a and the second light source 11b. The first light source 11a emits light of a first wavelength range, for example, wavelength greater than 600 nm and below 1,100 nm. The second light source 11b emits light of a second wavelength range that is shorter than that of the first light source 11a, for example, wavelength greater than 480 nm and below 560 nm. Light of the first wavelength range may be, for example, red light or infrared light and light of the second wavelength range may be green light. The first wavelength range and the second wavelength range may not be completely different from each other but some of them may overlap.

The power management module 34 allows the first light source 11a and the second light source 11b to emit light at different times. For example, the power management module 34 allows the first light source 11a and the second light source 11b to emit light alternately. Accordingly, the first light source 11a and the second light source 11b intermittently emit light and the light-emitting cycles are the same but the phases are different from each other.

The first light source 11a and the second light source 11b are adjacently disposed to each other. The first light source 11a and the second light source 11b radiate light toward almost the same part of a living body. The light receiver 12 detects scattered light from the part of the living body on to which the light is radiated. The light receiver 12 has sensitivity with respect to light of the first and second wavelength ranges. That is, when the first light source 11a emits infrared light, the light receiver 12 may detect light of wavelength ranges from infrared light to green light. When the first light source 11a emits red light, the light receiver 12 may detect light of wavelength ranges from red light to green light.

When light is radiated onto a living body, obtained bio-information may be different because the light reaching depths are different according to the wavelengths. For example, there is high possibility that green light is scattered near a depth of thick skin surface. However, red light or infrared light is absorbed little in the living body and is easily transmitted through the living body. When red light or infrared light is used, the amount of scattered light is increased in an artery. Since a reaching depth of red light or infrared light is deep, much information may be obtained. However, fat or peripheral blood vessels present in an epidermis or a thick skin besides the artery is small in amount, but affects as noise. This noise makes difficult to interpret the scattered light, and interrupts the obtainment of a precise bio-information. However, since green light has a low light reaching depth, noise due to scattered light by fat is little.

In the current exemplary embodiment, green light and red light or infrared light having a wavelength longer than that of green light are distinguishably used. More specifically, light (red light or infrared light) of a first wavelength range is used in a first duration of a single pulse wave, and light (green light) of a second wavelength range is used in a second duration. The sensor 10 controls to alternately emit light of a first wavelength range and light of a second wavelength range. Accordingly, it is possible to perform a measurement at different wavelengths with a simple configuration.

Figure 7:
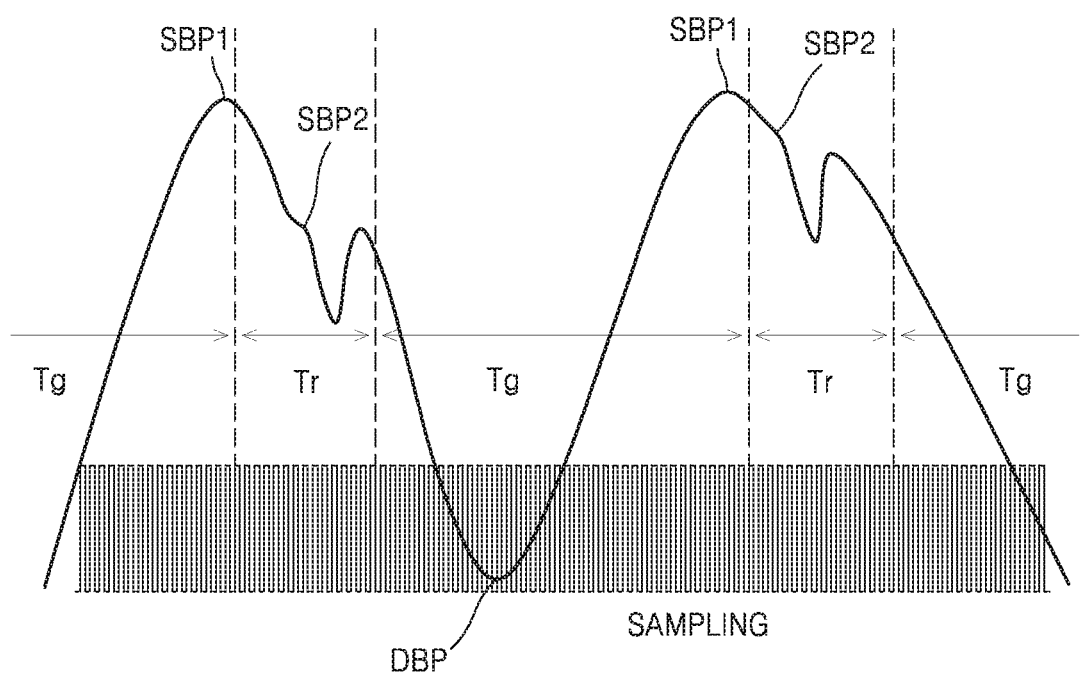
FIG. 7 is a graph for explaining a first duration and a second duration of one cycle of a pulse wave by a blood pressure measuring apparatus according to another exemplary embodiment.

The emission timing of the first light source 11*a* and the second light source 11*b* will be described with reference to FIG. 7. FIG. 7 is a graph for explaining light emission timing at a pulse wave. A single pulse wave may be divided into a first duration Tr and a second duration Tg. The first duration Tr is an emission time for emitting red light or infrared light. In the first duration Tr, the first light source 11*a* is turned on and the second light source 11*b* is turned off. The second duration Tg is an emission time for emitting green light. In the second duration Tg, the first light source 11*a* is turned off and the second light source 11*b* is turned on. The first duration Tr and the second duration Tg are repeated. Light of the first wavelength range and light of the second wavelength range are received by the light receiver 12. The ADC 23 converts the detected signal that is detected at a predetermined frequency to a digital value.

The second duration Tg includes a maximum value and a minimum value of a pulse wave. That is, the second duration Tg is a duration that includes a feature point (maximum value) based on a SBP1 and a feature point (minimum value) based on a DBP. In the second duration Tg, a timing before the minimum value is set as a start point and a timing after the maximum value is set as an end point. In the first duration Tr, the end timing of the second duration Tg is set as a start timing. The first duration Tr is a duration that is continued for a predetermined time from the end timing of the second duration Tg. An end timing of the first duration Tr is the start timing of the second duration Tg. The first duration Tr is a duration that includes a feature point based on a SBP2. In FIG. 7, the second duration Tg is longer than the first duration Tr. However, the second duration Tg may be shorter than the first duration Tr.

The maximum value and minimum value of a single pulse wave may be readily extracted. Accordingly, although green light that has weak intensity of light scattered from an artery is used, feature points based on an SBP1 and a DBP may be readily extracted. However, the feature point based on the SBP2 may be referred to as a minimal value, a maximal value, and an inflection point, and is difficult to extract. Accordingly, light of a first wavelength range is used for extracting the feature point of the SBP2. In a light of the first wavelength range, the intensity of scattered light at an artery is high, and thus, a feature point of the SBP2 may be easily expressed as the maximal value. The signal processing device 30 relatively readily extracts a feature point corresponding to the SBP2.

In the current exemplary embodiment, in the first duration Tr that includes a feature point of an SBP2, light of a first wavelength range is detected. The signal processing device 30 extracts a feature point of an SBP2 according to the light of a first wavelength range. In other words, the feature point of the SBP2 is extracted without using light of the second wavelength range. When light of the first wavelength range is used, the intensity of scattered light is increased, and thus, the feature point of the SBP2 may be readily extracted. For example, in order to extract the SBP2, it is unnecessary to differentiate a pulse wave twice or to interpret other data.

An example of processing method for extracting a feature point of an SBP2 will be described. Subtraction values from data neighboring each other are obtained by using data of the first duration Tr in one cycle of a pulse wave. Next, a duration in which the subtraction values near 0 appear is extracted by taking absolute values of the subtraction value. When counting the duration from the beginning of the cycle, it is possible that a time corresponding to a second time within the duration, in which many subtraction values near 0 appear, may be regarded as the R. Time, and data near the time may be regarded as an SBP2. In this manner, a feature amount of the SBP2 is obtained.

Also, the signal processing device 30 extracts a maximum value and a minimum value of a pulse wave based on light of a second wavelength range. A feature point based on an SBP1 and a feature point based on a DBP are extracted without using light of a first wavelength range. The extraction of a maximum value and a minimum value of a pulse wave is easy. Also, noise becomes small in green light. Accordingly, although green light that has a low intensity of scattered light at an artery is used, the signal processing device 30 may precisely extract the feature point.

Like in the exemplary Embodiment 1, the signal processing device 30 calculates a blood pressure from the feature points. The signal processing device 30 obtains a feature amount from a plurality of feature points extracted from a single pulse wave. Next, the signal processing device 30 converts the feature amount to a blood pressure by using a linear regression. The regression curve may be set by a data base when light of a first wavelength range and light of a second wavelength range are used. That is, after constructing the data base in which feature amounts and a pulse wave measurement correspond to each other when light of a first wavelength range and light of a second wavelength range are alternately radiated, and linear regression may be obtained by using this data base.

With respect to n cycles (n is an integer greater than 2) of a pulse wave, the signal processing device 30 calculates a feature amount on every cycle. By these method, n numbers of blood pressures are obtained. The n numbers of blood pressure values are averaged by using n as a parameter. In this manner, a blood pressure may be precisely measured.

Also, as in the exemplary Embodiment 1, a pulse wave from which a feature point may not be extracted or pulse wave that has a feature amount largely different from other pulse waves may be excluded from the calculation of a blood pressure. In the current exemplary embodiment, a feature point of an SBP2 is extracted by a detected signal that is detected based on a light of a first wavelength range. Accordingly, the feature point of the SBP2 may be precisely extracted. A pulse wave from which a feature point of an SBP2 may not be extracted or a pulse wave that has a feature point of the SBP2 largely different from other pulse waves may be excluded from the calculation of a blood pressure. Accordingly, a blood pressure may be precisely measured in a short time.

Furthermore, the AI value may be obtained by using the feature point of the SBP2. For example, on a wrist, the AI value may be obtained from the following equation.

$$AI = SBP2/SBP1(\text{peak point of a pulse wave}) \times 100$$

Regarding the setting of the first duration Tr and the second duration Tg, the first duration Tr and the second duration Tg may be appropriately set after measuring a plurality of pulse waves. For example, after measuring a plurality of pulse waves of a measurement subject, the signal processing device 30 may obtain a cycle of the pulse wave. Next, the signal processing device 30 may obtain information of times when a maximum value and a minimum value of a cycle are reached in every pulse wave. Next, a duration that includes the maximum value and the minimum value is set as a second duration, and a duration besides the second duration is set as a first duration.

In the current exemplary embodiment, light of a different wavelength range is used in a single pulse wave. That is, a single pulse wave is divided into a first duration and a second duration, and lights of different wavelength ranges respectively are used during the first duration and the second duration. In this manner, a feature point may be precisely extracted. In particular, a feature point of an SBP2 may be readily extracted. Accordingly, a blood pressure may be accurately measured.

Furthermore, since the first light source 11a and the second light source 11b alternately emit light, the light receiver 12 outputs both a first detected signal based on the first wavelength range and a second detected signal based on the second wavelength range. That is, the single light receiver 12 outputs the first detected signal based on the first wavelength range with respect to the first duration Tr and outputs the second detected signal based on the second wavelength range with respect to the second duration Tg. In this way, since the blood pressure measuring apparatus 1 includes a single light receiver 12 and a single AFE 20, the configuration of the blood measuring apparatus may be simplified.

Also, in the above descriptions, the first and second light sources 11a and 11b having different light colors are installed. Accordingly, two light receivers 12 may be installed. That is, a first light receiver that receives light of a first wavelength range and a second light receiver that receives a second wavelength range may be installed in the sensor 10. In other words, a first light receiver that does not have sensitivity to the second wavelength range and a second light receiver that does not have sensitivity to the first wavelength range may be installed. Also, one light source that emits lights of first and second wavelength ranges and two light receivers respectively receive the first and second wavelength ranges may be installed. In this case, a light source may be a white light source. Alternatively, two light sources and two light receivers may be installed. At this point, a first light source and a first light receiver that correspond to the first wavelength range, and a second light source and a second light receiver that correspond to the second wavelength range may be installed.

In the exemplary Embodiment 2, the digital process for removing noise from a detected signal by using the digital filter 33 shown in the exemplary Embodiment 1 may not be performed. That is, as described in the exemplary Embodiment 1, a feature point may be extracted based on a subtraction value of two moving averages, and alternately, a feature point may be extracted based on a detected signal that is not digital processed.

The blood pressure measuring apparatus 1 according to the exemplary Embodiments 1 and 2 may be mounted on a wearable terminal, such as a wrist watch terminal. The blood pressure measuring apparatus 1 may be referred to as a wrist watch terminal. Since the sensor 10 on the wrist watch terminal may include a wireless communication unit, other elements (for example, the signal processing device 30, the display 40, etc) may be mounted on a smart phone. In this case, analog data or digital data obtained by the wrist watch terminal is transmitted to the smart phone via the wireless communication. The smart phone that receives the data may perform a partial or an entire processing for measuring a blood pressure.

In a blood pressure measuring apparatus according to an exemplary embodiment and a method of measuring a blood pressure, noise may be removed by using a subtraction value of moving average values, and thus, a high precision blood measurement is possible.

In a blood pressure measuring apparatus according to another exemplary embodiment and a method of measuring a blood pressure, a feature point of an SBP2 is calculated by using a first wavelength that is appropriate for measuring the SBP2, and a maximum blood pressure is calculated by calculating a feature point from which noise is reduced by using a second wavelength which is longer than the first wavelength, and thus, a high precision blood measurement is possible.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure measuring apparatus comprising:
a sensor comprising a light source configured to emit light onto a living body and a light receiver configured to receive light from the living body, the received light carrying a first detection signal and a second detection signal and being represented as a pulse wave; and
a processor configured to extract a first feature point and a second feature point of the pulse wave based on the first detection signal and the second detection signal and convert a feature amount of the pulse wave to a blood pressure value based on the extracted first feature point and the extracted second feature point of the pulse wave,
wherein the light source is further configured to output the first detection signal based on light of a first wavelength range and the second detection signal based on light of a second wavelength range that is shorter than the first wavelength range, and
the processor is further configured to:
during a feature extraction cycle, extract the first feature point based on a systolic blood pressure (SBP) that is based on the first detection signal in a first duration of the pulse wave, and extract the second feature point based on the second detection signal in a second duration which is a duration different from the first duration, while the sensor is continuously receiving the first detection signal and the second detection signal, by setting a starting point of the feature extraction cycle to a time when a subtraction of a second moving average value of the second detection signal from a first moving average value of the first detection signal changes from a negative value to a positive value, and setting an end point of the feature extraction cycle to a time when the subtraction changes back to the negative value from the positive value, and convert the feature amount into the blood pressure value based on the first and second feature points.

2. The blood pressure measuring apparatus of claim 1, wherein the second feature point comprises a maximum value and a minimum value of the pulse wave.

3. The blood pressure measuring apparatus of claim 1, wherein the light of the first wavelength range is red light or infrared light, and the light of the second wavelength range is green light.

4. The blood pressure measuring apparatus of claim 1, wherein the light source is further configured to alternately emit the light of the first wavelength range during the first duration and the light of the second wavelength range during the second duration.

5. A method of measuring blood pressure by using a blood pressure measuring apparatus that includes a sensor including a light source that emits light onto a living body, and a light receiver that receives light from the living body, the received light carrying a first detection signal and a second detection signal and being represented as a pulse wave, and a processor that extracts a first feature point and a second feature point of the pulse wave based on the first detection signal and the second detection signal received from the sensor, and converts feature amounts based on the first feature point and the second feature point to a blood pressure value, the method comprising:

outputting the first detection signal based on light of a first wavelength range and the second detection signal based on light of a second wavelength range which is shorter than the first wavelength range;

during a feature extraction cycle, extracting the first feature point of the pulse wave in a first duration of a cycle of the pulse wave based on a systolic blood pressure (SBP) that is obtained based on the first detection signal, and extracting the second feature point based on the second detection signal in a second duration that is different from the first duration in the cycle, while the sensor is continuously receiving the first detection signal and the second detection signal, by setting a starting point of the feature extraction cycle to a time when a subtraction of a second moving average value of the second detection signal from a first moving average value of the first detection signal changes from a negative value to a positive value, and setting an end point of the feature extraction cycle to a time when the subtraction changes back to the negative value from the positive value; and converting amounts corresponding to the first and second feature points to the blood pressure value.

6. The method of claim 5, wherein the second feature point comprises a maximum value and a minimum value of the pulse wave.

7. The method of claim 5, wherein the light of the first wavelength range is red light or infrared light, and the light of the second wavelength range is green light.

8. The method of claim 7, wherein the outputting the first detection signal comprises using the light of the first wavelength range during the first duration, using the light of the second wavelength range during the second duration, and alternately using the light of the first wavelength range and the light of the second wavelength range.

9. The method of claim 5, wherein the extracting the second feature point comprises, in selecting the feature extraction cycle from a plurality of feature extraction cycles, excluding a cycle from which at least one of a maximal value and a minimal value is not extracted due to noise.

* * * * *